United States Patent [19]

Larsson

[11] Patent Number: 4,621,195
[45] Date of Patent: Nov. 4, 1986

[54] APPARATUS FOR DESTROYING MICROORGANISMS

[75] Inventor: Lars P. Larsson, Eskilstuna, Sweden

[73] Assignee: L. P. Larsson AB, Eskilstuna, Sweden

[21] Appl. No.: 679,045

[22] PCT Filed: Mar. 29, 1984

[86] PCT No.: PCT/SE84/00116

§ 371 Date: Nov. 20, 1984

§ 102(e) Date: Nov. 20, 1984

[87] PCT Pub. No.: WO84/03880

PCT Pub. Date: Oct. 11, 1984

[30] Foreign Application Priority Data

Mar. 30, 1983 [SE] Sweden ............................. 8301762

[51] Int. Cl.$^4$ ..................... G01N 21/01; H01J 37/16
[52] U.S. Cl. ..................... 250/438; 250/436; 250/437; 250/455.1
[58] Field of Search ............ 250/436, 437, 438, 455.1, 250/432 R; 422/24, 22

[56] References Cited

U.S. PATENT DOCUMENTS

| 1,196,481 | 3/1916 | Von Recklinghauser et al. ........................... 250/437 |
| 1,200,940 | 10/1916 | Henri et al. ................... 250/437 |
| 1,266,803 | 5/1918 | Henri et al. . |
| 1,473,095 | 11/1923 | Henri et al. . |
| 1,486,473 | 3/1924 | Ailhaud . |
| 2,065,055 | 12/1936 | Berndt et al. ...................... 250/437 |
| 3,079,498 | 2/1968 | Ruffin . |
| 4,008,045 | 2/1977 | Free . |
| 4,151,090 | 4/1979 | Brigante . |
| 4,278,549 | 7/1981 | Abrams et al. . |

FOREIGN PATENT DOCUMENTS

| 26659/63 | 6/1965 | Australia . |
| 25223/67 | 2/1969 | Australia . |
| 68115/74 | 12/1974 | Australia . |
| 61286/73 | 4/1975 | Australia . |
| 258685 | 4/1913 | Fed. Rep. of Germany . |
| 278368 | 9/1914 | Fed. Rep. of Germany . |
| 1167578 | 10/1969 | United Kingdom . |

Primary Examiner—Bruce C. Anderson
Attorney, Agent, or Firm—Pennie & Edmonds

[57] ABSTRACT

Apparatus for destroying microorganisms by irradiation with ultra-violet light from a UV-lamp in a major irradiation chamber. The major chamber is divided into minor chambers by means of partition walls. The walls are provided with through-flow openings at their alternate ends whereby the bacteria-carrying medium is conducted reciprocatingly along the UV-lamp and thereby subjected to intensive radiation therefrom over a relatively long period of time.

7 Claims, 3 Drawing Figures

APPARATUS FOR DESTROYING MICROORGANISMS

Such material as liquids (water) and gases (air) can be cleansed of undesirable microorganisms by irradiation with ultra-violet light of wave-lengths shorter than 320 nm. Irradiation is effected with the aid of a so-called ultra-violet lamp. The present invention has been developed in conjunction with such bacteria-destroying apparatus.

In order to destroy bacteria efficiently, it is necessary to expose the treated material to radiation from a UV lamp over a long period of time. The longer the exposure time, the greater the effectiveness in destroying bacteria. In order to obtain an effective exposure time, the radiation chamber may incorporate either a single long UV-tube or a plurality of shorter tubes. This latter alternative, however, increases plant costs to an unacceptable level. It is the problem of plant costs which has engendered the present invention.

SUMMARY OF THE INVENTION

Apparatus for destroying microorganisms by irradiation with ultra-violet light from a UV-lamp in a major irradiation chamber. The major chamber is divided into minor chambers by means of partition walls. The walls are provided with through-flow openings at their alternate ends whereby the bacteria-carrying medium is conducted reciprocatingly along the UV-lamp and thereby subjected to intensive radiation therefrom over a relatively long period of time.

The apparatus will now be described with reference to the accompanying drawings, in which FIG. 1 is a perspective view of an irradiation chamber;

Figure 1:
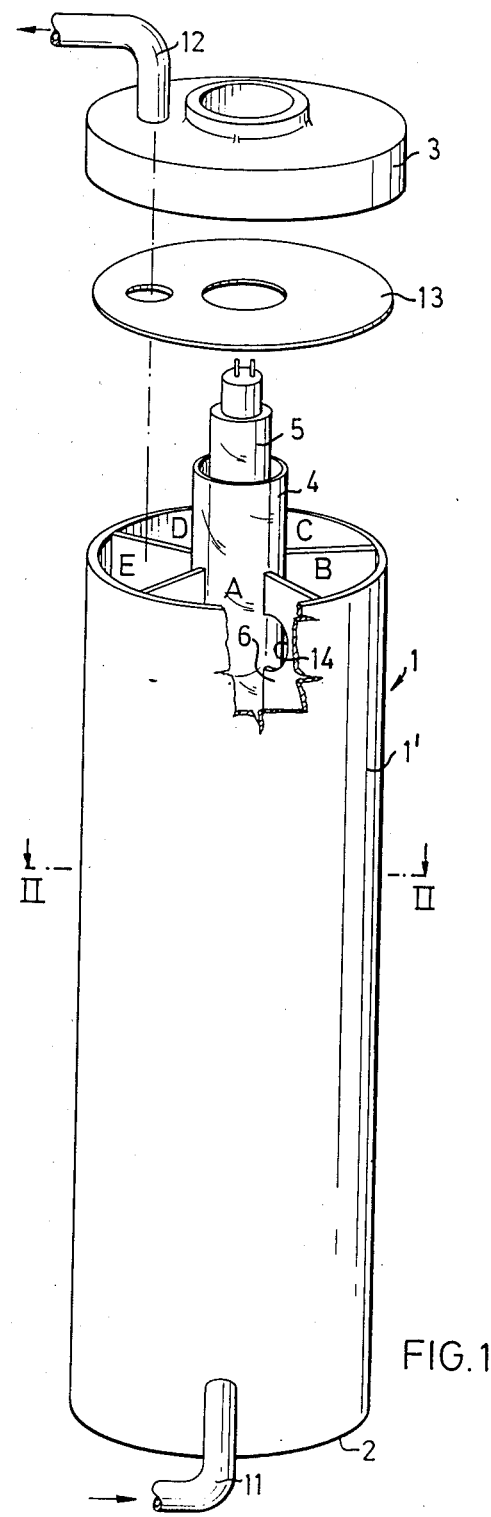
Figure 2:
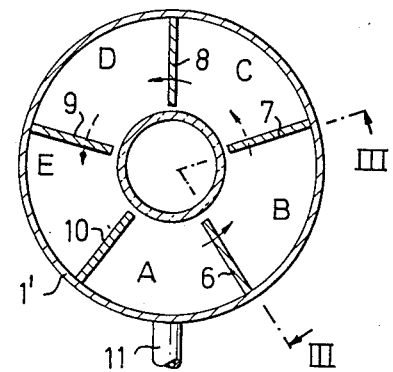
FIG. 2 is a horizontal sectional view taken on the line II—II in FIG. 1.
Figure 3:
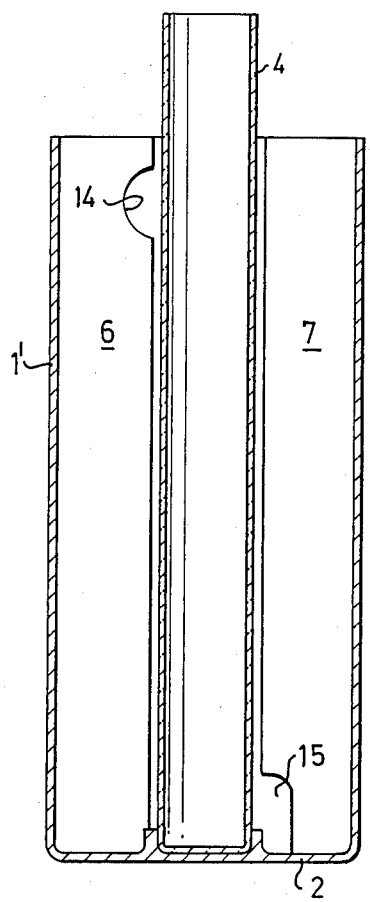
FIG. 3 is a longitudinal sectional view taken on the line III—III in FIG. 2.

Since in principle, the apparatus can be used to treat both liquids and gases, there will be first described a plant for treating liquids, followed by a description of a gas-treating plant.

IRRADIATION OF LIQUIDS

The irradiation chamber, also known as a UV-chamber, comprises a substantially vertically arranged cylindrical vessel 1, the cylinder wall 1' of which is sealed at both ends; at the bottom by means of a permanent wall 2 and at the top by means of a tightly fitting cap 3 provided with requisite sealing means. The irradiation chamber is made of a material suitable for ultra-violet radiation.

Placed in a known manner centrally of the chamber is a quartz-crystal glass tube 4 having a UV-lamp 5 arranged therein. The quartz-crystal glass tube is completely sealed at the bottom thereof, and extends substantially to the bottom 2 of the chamber 1, where it is anchored in a known manner. The quartz-crystal glass tube 4 extends upwardly through the cap 3, which is provided with suitable sealing means not shown.

The UV-lamp 5 is mounted within the quartz-crystal glass tube 4, and the length dimensions of the lamp are substantially the same as those of the glass tube 4. The UV-lamp 5 is connected to a lamp holder in a known manner, not shown. Neither are those electrical connections shown which are known or which are not directly associated with the concept of the invention. The quartz-crystal glass tube 4 together with the UV-lamp 5 can be readily mounted in position and dismantled when it is necessary to clean, primarily, the quartz-crystal glass tube. The UV-lamp can be changed in the normal fashion.

The radiation chamber 1 can be provided, in a known manner, with a photocell arranged to function as a signal guard and a means for monitoring purification.

In accordance with the invention there is arranged within the radiation chamber 1 five vertical walls 6, 7, 8, 9 and 10. The walls 6–10 extend radially in the chamber 1 and are sealingly connected to the cylinder wall 1', and the bottom wall 2 thereof. The tops of the walls are sealingly connected to the cap 3 of the chamber 1 through the agency of separate sealing means, such as the illustrated seal 13 for example. An annular gap has been left between the walls 6–10 inclusive and the quartz-crystal glass tube 4, to facilitate assembly and dismantling of the radiation chamber.

In this way, in the illustrated embodiment the major irradiation chamber has been divided into five minor irradiation chambers, referenced A,B,C,D and E on the drawing.

Arranged in the upper part of wall 6 is an opening 14, which connects the chamber A with Chamber B. A similar opening 15 connecting chamber B with chamber C is arranged in the lower part of the wall 7. The openings 14 and 15 are located adjacent the tube 4 and preferably extend radially no further from said tube than a limited part of the radial distance from the tube 4 to the cylinder wall 1'. The partition wall 8 has an upper opening 14 similar to that of the wall 6, while the partition wall 9 has a lower opening 15, similar to that of the wall 7. There is no connection in the partition wall 10 affording communication between mutually adjacent chambers A and E.

Arranged in the lower part of the major chamber 1 is a connection or inlet 11, which communicates with the Chamber A. An outlet 12 communicating with the chamber E is arranged in the upper part of the major chamber 1, in the illustrated embodiment the outlet 12 is located in the cap 3.

OPERATIONAL MODE

The liquid to be irradiated with ultra-violet rays is passed through the inlet 11 and into the chamber A. As a result of the connection 14 of chamber A with chamber B, the liquid in chamber A will travel upwards, while as a result of the bottom connection 15 of chamber B with chamber C, the liquid in chamber B will move downwards. The liquid in chamber C will again move in an upward direction, as a result of the connection between the chambers C and D, while the liquid in chamber D will move downwards, as a result of the bottom connection between the chambers D and E. Liquid in the chamber E will move upwardly therein and exit through the outlet 12 connected therewith.

In order to ensure that the major chamber is filled satisfactorily along substantially the whole of its height or length, the inlet 11 is suitably located in the lower part of the major chamber 1 and the outlet 12 in the upper part thereof, such as to ensure total filling of said chamber. This arrangement requires the number of partition walls provided to be an odd number.

As a result of the aforedescribed arrangement, in which liquid is passed reciprocatingly along the quartz-crystal glass tube 4 housing the UV-lamp 5, the liquid will be exposed to the ultra-violet rays emitted by the lamp 5 for a relatively long period of time. A minor part of the liquid will escape from the main flow and pass through the narrow gap between the glass tube 4 and the adjacent ends of the partition walls, and will not therefore accompany the main flow in its circuitous path through the apparatus. This lacks significance, however, since the liquid which escapes will have been effectively irradiated with ultra-violet rays, partly because of the small volume involved and partly because of the intense radiation to which said volume liquid is subjected as a result of its closeness to the actual UV-lamp.

The plant may be operated intermittently. When the plant is started up, there will be a certain delay before the UV-lamp 5 has full effect. Consequently, it is essential that the flow of liquid has a relatively long path to travel along the UV-lamp 5, so as to obtain the intended exposure time. That liquid found adjacent the outlet 12 and deriving from an immediately preceding, terminated working operation has earlier been exposed to a full dosage of radiation, from the lamp 5.

IRRADIATION OF GASES

In principle, the same apparatus as that used to irradiate liquids with ultra-violet rays can also be used to irradiate gases.

In the case of gases, the major irradiation chamber 1 can be oriented in any desired direction. Since gas will naturally pervade the irradiation chamber, to completely fill said chamber, the inlet and outlet can be optionally placed on mutually opposite sides of the irradiation chamber 1, or on the same side thereof. This enables the provision of any desired number of partition walls.

In other respects, the operational mode of the plant in respect of gases is the same as that previously described in respect of liquids.

VARIANT EMBODIMENT

The major irradiation chamber 1 may also be provided with sealing means between the quartz-crystal glass tube 4 and each partition wall, from 6 to 10 inclusive. The aforedescribed communication parts between the minor chambers are retained.

This embodiment enables the major irradiation chamber 1 to be oriented in any desired direction. Similarly, there is afforded a freedom of choice with respect to the number of minor chambers (A to E) provided, allowing the inlet and outlet to be placed on one and the same side or on mutually opposite sides. The arrangement always ensures that the major chamber is completely filled.

The aforedescribed embodiments merely constitute examples of the invention and can be modified within the scope of the following claims. For example, the major irradiation chamber may have a different shape to the illustrated circular-cylindrical shape, for example a hexagonal or an octagonal shape. The number of partition walls provided may be different from five, even in the case of a circular-cylindrical major chamber. The guard around the lamp may be of some other design, or optionally the lamp may be used without a separate guard.

I claim:

1. Apparatus for destroying microorganisms in a bacteria-containing medium, by treating said medium with bacteria-destroying ultra-violet radiation, in which the medium is passed from an inlet (11) in an irradiation chamber (1), past a UV-lamp (5), which is preferably protected by a quartz-crystal glass tube (4), to an outlet (12), characterized in that a major irradiation chamber (1) is divided into a plurality of mutually co-acting minor chambers (A, B, C, D and E) so arranged in the lengthwise direction along the length of said UV-lamp so that during its passage through the major chamber (1), the through-flowing medium is caused to travel reciprocatingly along the UV-lamp (5) in a manner to subject the bacteria-carrying medium to a relatively long and intensive period of radiation from the UV-lamp (5), and in that the respective walls (6–9) between the mutually co-acting minor chambers (A, B, C, D and E) are alternatively provided with upper and lower connection openings (14,15) located in the radially innermost part of said walls nearest the UV-lamp (5), such that during the course of its reciprocating movement said through-flowing medium is forced to flow along the UV-lamp (5) and is also transported therearound.

2. Apparatus according to claim 1, characterized in that the radially enner edges of the partition walls (6–9) terminate at a location adjacent the UV-lamp (5), or the protective tube (4), in the absence of seals therebetween, such as to permit a minor flow of medium in the gap thus formed.

3. Apparatus according to claim 2, characterized in that when treating liquids said apparatus preferably incorporates an odd number of minor chambers, said inlet (11) and said outlet (12) being located on mutually opposite sides.

4. Apparatus according to claim 1 or claim 2 for treating gas, characterized in that said apparatus incorporates either an odd or an even number of minor chambers (A–E); and in that positioning of the inlet (11) and outlet (12) is dependent upon whether an odd or an even number of walls is provided.

5. Apparatus according to claim 1 or claim 2, characterized in that seals are arranged between the partition walls (6,7,8,9 and 10) and the UV-lamp (5) or the quartz-crystal protective tube (4), wherewith any number of minor chambers (A, B, C, D and E) can be selected; the number of minor chambers provided determining the positioning of the inlet (11) and the outlet (12) with respect to one another.

6. Apparatus for destroying microorganisms in a bacteria-containing medium by treating said medium with bacteria-destroying ultra-violet radiation, in which said medium is passed from an inlet in an irradiation chamber, past an elongated UV-lamp, to an outlet; wherein said irradiation chamber is divided into a plurality of mutually co-acting minor chambers by partition walls spaced around the UV lamp and extending in the lengthwise direction along the length of said UV-lamp, and wherein said partition walls are provided with openings connecting said minor chambers to each other, which openings alternatively are located in the lengthwise direction at opposite end sections of said walls, so that said bacteria-containing medium during its movement from inlet to outlet of said irradiation chamber in said minor chambers is caused to travel back and forth along the length of said UV-lamp and around said UV-lamp as it travels from one minor chamber to another for subjecting said medium to a relatively long period of intensive UV-radiation.

7. Apparatus for destroying microorganisms in a bacterial-containing medium by treating said medium with ultra-violet radiation, in which apparatus said medium is passed from an inlet in an irradiation chamber, past an elongated UV-lamp, to an outlet; wherein the irradiation chamber is divided into a plurality of mutually co-acting minor chambers by partition walls spaced around the UV-lamp and extended in the lengthwise direction therealong over the whole length of the irradiation chamber (1) and sealingly connected to the walls (1', 2, 3) thereof; openings (14, 15) successively connecting the minor chambers (A-E) to each other are provided in the partition walls (6-9) between co-acting minor chambers in the radially innermost part of the respective wall near the UV-lamp (5), which openings alternatively are located at opposite end sections of the partition walls, and the inlet (11) and outlet (12) of the irradiation chamber are located in adjacent minor chambers (A, E), whereby said medium during its flow from inlet to outlet is caused to successively pass through each of the minor chambers flowing back and forth along the length of the UV-lamp and around the whole circumference thereof.

* * * * *